United States Patent [19]

Quincy, III et al.

[11] Patent Number: 5,614,295
[45] Date of Patent: Mar. 25, 1997

[54] LIQUID DISTRIBUTION AND RETENTION MEDIUM

[75] Inventors: Roger B. Quincy, III, Alpharetta; Debra J. McDowall, Roswell; Elizabeth D. Gadsby, Marietta, all of Ga.; Alice Y. Romans-Hess, Freemont; Garry R. Woltman, Neenah, both of Wis.

[73] Assignee: Kimberly-Clark Corporation, Neenah, Wis.

[21] Appl. No.: 361,392

[22] Filed: Dec. 21, 1994

[51] Int. Cl.⁶ .................................................. B32B 7/02
[52] U.S. Cl. .......................... 428/212; 427/533; 427/535; 427/536; 427/562; 428/409; 428/543; 428/903; 428/447
[58] Field of Search ................... 428/409, 411.1, 428/543, 903, 212, 447; 427/533, 535, 536, 538, 562

[56] References Cited

U.S. PATENT DOCUMENTS

| | | | |
|---|---|---|---|
| 3,661,735 | 5/1972 | Drelich | 204/165 |
| 3,880,966 | 4/1975 | Zimmerman et al. | 264/25 |
| 3,997,647 | 12/1976 | Lassen | 264/178 |
| 4,110,143 | 8/1978 | Cogliano et al. | 156/167 |
| 4,275,105 | 6/1981 | Boyd et al. | 428/198 |
| 4,456,570 | 6/1984 | Thomas et al. | 264/22 |
| 4,469,746 | 9/1984 | Weisman et al. | 428/289 |
| 4,535,020 | 8/1985 | Thomas et al. | 428/131 |
| 4,650,479 | 3/1987 | Insley | 604/358 |
| 4,663,220 | 5/1987 | Wisneski et al. | 428/221 |
| 4,714,647 | 12/1987 | Shipp, Jr. et al. | 428/212 |
| 4,865,596 | 9/1989 | Weisman et al. | 604/368 |
| 4,910,064 | 3/1990 | Sabee | 428/113 |
| 4,920,168 | 4/1990 | Nohr et al. | 524/188 |
| 4,933,229 | 6/1990 | Insley et al. | 428/224 |
| 4,965,122 | 10/1990 | Morman | 428/225 |
| 5,051,159 | 9/1991 | Togashi et al. | 204/165 |
| 5,093,197 | 3/1992 | Howard et al. | 428/372 |
| 5,102,738 | 4/1992 | Bell et al. | 428/411.1 |
| 5,112,690 | 5/1992 | Cohen et al. | 428/411.1 |
| 5,200,248 | 4/1993 | Thompson et al. | 428/131 |
| 5,244,723 | 9/1993 | Anderson et al. | 428/283 |
| 5,352,480 | 10/1994 | Hansen et al. | 427/202 |

FOREIGN PATENT DOCUMENTS

| | | |
|---|---|---|
| 0483859 | 5/1992 | European Pat. Off. . |
| 0564784 | 10/1993 | European Pat. Off. . |
| 93/11727 | 6/1993 | WIPO . |

OTHER PUBLICATIONS

Copy of Search Report for PCT/US95/16623 dated Aug. 14, 1996.

*Primary Examiner*—James J. Bell
*Attorney, Agent, or Firm*—William E. Maycock

[57] ABSTRACT

A fibrous web which includes a first zone composed of fibers which have been treated with a surfactant and a second zone composed of fibers which have been exposed to a corona field. At least one of the first zone and the second zone constitutes less than all of the fibrous web. In addition, the fibers constituting the second zone also constitute a portion of the fibers of the first zone. The first zone and the second zone may involve essentially the same portion of the fibrous web, provided that both zones do not encompass the entire fibrous web. Both the first zone and the second zone may constitute less than all of the fibrous web. In certain embodiments, the fibrous web will be composed of fibers which are at least partially oriented in one direction. Either the first zone or the second zone may encompass all of the fibrous web. That is, the entire fibrous web may treated with a surfactant or exposed to a corona field. Desirably, the entire fibrous web will be treated with a surfactant. Alternatively, the fibers of the second zone may be the same fibers of which a portion of the first zone is composed. The fibrous web may be employed as a component of such absorbent product as diapers; incontinent care products; and feminine care products, such as sanitary napkins and tampons.

23 Claims, 6 Drawing Sheets

LIQUID DISTRIBUTION AND RETENTION MEDIUM

BACKGROUND OF THE INVENTION

The present invention relates to a liquid distribution and retention medium, particularly a liquid distribution and retention medium which is a component of an absorbent product.

Absorbent products currently find wide-spread applications, many of which are intended for limited or even single use. Typical of such products are diapers; incontinent care products; feminine care products, such as sanitary napkins and tampons; filter elements; wipes; surgical gowns and drapes; protective pads; wound dressings, such as bandages; and the like. A number of these products have an absorbent core which is covered by a layer of fabric, often a nonwoven web, commonly referred to as the liner or body-side layer. For body-contacting products, the liner usually is adjacent to the skin.

Many absorbent products are concerned with, at least to some degree, such factors as the distribution, capacity, and retention of a liquid. Liquid distribution, capacity, and retention are of concern because they affect, to a greater or lesser extent, the ability of the product to absorb liquid without leakage. They also have an effect on aesthetic qualities, such as appearance, particularly during and after use.

Liquid distribution, sometimes referred to as wicking, generally involves the movement of liquid away from the locus of liquid insult to the remainder of the absorbent product. Distribution, in effect, makes more of the absorbent product available for absorption of liquid. Retention is of interest because it contributes to reduced leakage. Consequently, improving liquid distribution and retention have, in the past, involved a significant research and development effort. Nevertheless, opportunities remain for additional improvements in both liquid distribution and retention.

SUMMARY OF THE INVENTION

The present invention addresses some of the difficulties and problems discussed above by providing a liquid distribution and retention medium. The medium is a fibrous web which includes a first zone composed of fibers which have been treated with a surfactant and a second zone composed of fibers which have been exposed to a corona field. At least one of the first zone and the second zone constitutes less than all of the fibrous web. In addition, the fibers comprising the second zone also comprise a portion of the fibers of the first zone. Also, in some embodiments, both the first zone and the second zone may constitute less than all of the fibrous web.

In certain embodiments, the fibrous web will be composed of fibers which are at least partially oriented in one direction. That is, the fibrous web will have a fiber alignment ratio as defined hereinafter of at least about 2:1. For example, the fibrous web may be a meltblown nonwoven web. As another example, the fibrous web may be a neck-stretched meltblown nonwoven web.

Either the first zone or the second zone may encompass all of the fibrous web. That is, the entire fibrous web may be treated with a surfactant or exposed to a corona field. Desirably, the entire fibrous web will be treated with a surfactant.

The fibers of which the second zone is composed may be essentially the same fibers of which the first zone is composed. In other words, the first zone and the second zone may involve essentially the same portion of the fibrous web, provided, of course, that both zones do not encompass the entire fibrous web.

When the fibrous web is composed of fibers which are at least partially oriented in one direction, the web desirably is adapted to distribute liquid primarily in the direction of orientation of the fibers. For example, the distribution of liquid in the direction of orientation of the fibers may be at least about twice the distribution of liquid in a direction which is substantially normal to the direction of orientation of the fibers. In this case, the fibrous web is said to have a liquid distribution aspect ratio of at least about 2. As a further example, the distribution of liquid in the direction of orientation of the fibers may be greater than about three times the distribution of liquid in a direction which is substantially normal to the direction of orientation of the fibers; i.e., the web may have a liquid distribution aspect ratio greater than about 3.

The fibrous web of the present invention also exhibits significantly increased liquid retention when compared with a similar web which lacks the second zone. In general, the fibrous web of the present invention will retain at least about 1.5 times as much liquid as a similar web which lacks the second zone. For example, the fibrous web may retain at least about twice as much liquid as the similar web. As another example, the fibrous web may retain at least about three times as much liquid as the similar web. As a further example, the fibrous web may retain at least about four times as much liquid as the similar web.

In general, any surfactant may be employed. For example, the surfactant may be adapted to have increased wettability characteristics as a result of exposure of surfactant-treated fibers to a corona field. Such surfactants include polyethoxylated alkyl-substituted phenols. Alternatively, the surfactant may be adapted to have an increased affinity for the fibers of which the fibrous web is composed as a consequence of first exposing the fibers to a corona field. Such surfactants include polysiloxane polyethers.

The present invention also provides a method of preparing a liquid distribution and retention medium which includes the steps of providing a fibrous web, treating at least a portion of the fibrous web with a surfactant to form a first zone composed of surfactant-treated fibers, and exposing a portion of the fibrous web to a corona field to form a second zone composed of fibers which have been exposed to a corona field. At least one of the first zone and the second zone constitutes less than all of the fibrous web and the fibers constituting the second zone also constitute a portion of the fibers of the first zone. Desirably, the fibers of which the fibrous web is composed will be at least partially oriented in one direction.

The present invention further provides a method of preparing a liquid distribution and retention medium which includes the steps of providing a fibrous web, exposing a portion of the fibrous web to a corona field to form a second zone composed of fibers which have been exposed to a corona field, and treating at least a portion of the fibrous web with a surfactant to form a first zone composed of surfactant-treated fibers. At least one of the first zone and the second zone constitute less than all of the fibrous web and the fibers constituting the second zone also constitute a portion of the fibers of the first zone. Again, the fibers of which the fibrous web is composed desirably will be at least partially oriented in one direction.

The fibrous web of the present invention may be employed as a component of such absorbent products as diapers; incontinent care products; and feminine care products, such as sanitary napkins and tampons. For example, the web may be employed as a distribution layer between an absorbent core and a liner or body-side layer.

DETAILED DESCRIPTION OF THE INVENTION

As used herein, the term "machine direction" means a direction which is essentially parallel with the motion of a web through the web-forming, e.g., meltblowing, apparatus as the web is formed; i.e., a direction which is parallel with the direction of the forming wire upon which the web is formed. The term "cross direction" is used herein to mean a direction which is the cross machine direction, i.e., a direction which is perpendicular to the machine direction.

The term "liquid" is used herein with its customary meaning. As a practical matter, the liquid most often will be an aqueous liquid. When the fibrous web of the present invention is employed in an absorbent product, the liquid typically will be bodily excrement, such as urine, blood, menses, serum, and the like.

As used herein, the "liquid distribution aspect ratio" (or "aspect ratio") is the ratio of the maximum movement of liquid which is essentially parallel with the direction of orientation of the fibers of which the fibrous web is composed to the maximum movement of liquid which is essentially normal to the direction of orientation of the fibers; it is determined by the blood wicking procedure or test described in the examples. Thus, the liquid distribution aspect ratio is the quotient of the maximum distance the liquid has traveled in a direction which is essentially parallel with the direction of orientation of the fibers, divided by the maximum distance the liquid has traveled in a direction which is essentially normal to the direction of orientation of the fibers. While the aspect ratio may be determined under any desired set of conditions, comparisons of aspect ratios require essentially the same set of conditions for each of the fibrous webs tested. Test conditions having the greatest impact on aspect ratio include the blood flow rate and the time of the test.

As used herein, the term "surfactant" includes a single surfactant or a mixture of two or more surfactants. If a mixture of two or more surfactants is employed, the surfactants may be selected from the same or different classes, provided only that the surfactants present in the mixture are compatible with each other. In general, the surfactant may be any surfactant known to those having ordinary skill in the art, including anionic, cationic, and nonionic surfactants. Examples of anionic surfactants include, among others, linear and branched-chain sodium alkylbenzenesulfonates, linear and branched-chain alkyl sulfates, and linear and branched-chain alkyl ethoxy sulfates. Cationic surfactants include, by way of illustration, tallow trimethylammonium chloride. Examples of nonionic surfactants, include, again by way of illustration only, alkyl polyethoxylates, polyethoxylated alkylphenols, fatty acid ethanol amides, complex polymers of ethylene oxide, propylene oxide, and alcohols, and polysiloxane polyethers.

The term "add-on" is used herein to indicate the amount of surfactant present on the fibers of a sample of a fibrous web; it is calculated as a percentage based on the original dry weight of the web sample as follows:

Percent add-on=100×(g SWS–g WS)/g WS wherein "g SWS" ("g Surfactant-Web Sample) refers to the dry weight of the sample to which the surfactant has been applied and "g WS" ("g Web Sample") refers to the dry weight of the original sample, i.e., the dry weight of the sample before being treated with a surfactant solution.

The liquid distribution and retention medium of the present invention is a fibrous web having a length, a width, and a thickness. The web includes a first zone composed of fibers which have been treated with a surfactant and a second zone composed of fibers which have been exposed to a corona field. At least one of the first zone and the second zone constitutes less than all of the fibrous web. In addition, the fibers constituting the second zone also constitute a portion of the fibers of the first zone.

In certain embodiments, the fibrous web will be composed of fibers which are at least partially oriented in one direction. That is, the web is formed in such a manner that more fibers are oriented in a given direction, e.g., the machine direction, than fibers oriented another direction, e.g., the cross direction. Fiber orientation may be expressed as the fiber alignment ratio which is determined by measuring the velocity of sound waves passing longitudinally through the fibrous web in both the machine direction and the cross direction, and estimating the sonic modulus in each direction, in accordance with ASTM Test Method F89-68, "Standard Method of Test for Modulus of a Flexible Barrier Materials by Sonic Method." The fiber alignment ratio then is calculated by dividing the sonic modulus in the machine direction by the sonic modulus in the cross direction. Thus, the fiber alignment ratio is the ratio of the sonic modulus in the machine direction to the sonic modulus in the cross direction.

By way of illustration, the fibrous web may be a nonwoven web prepared by a melt-extrusion process which at least partially orients fibers in one direction. Meltblowing is an example of such a process, in which case the direction of fiber orientation is in the machine direction. An average fiber alignment ratio for meltblown polypropylene nonwoven webs is about 2.

As another example, the fibrous web may be a neck-stretched meltblown nonwoven web. Neck-stretching is a procedure which increases the orientation of fibers in the direction of stretching with a concomitant reduction in the width of the web. The extent of neck-stretching may vary widely. As a practical matter, however, the extent of neck-stretching in general will be in a range of about 15 percent to about 75 percent. The percent of neck-stretching (PNS), as used herein, is calculated by dividing the difference in width between the initial sample (Widths) and the necked sample (Width$_f$) by the initial sample width (Width$_i$) and multiplying the quotient by 100:

PNS=100×((Width$_i$–Width$_f$)/Width$_i$

The procedure involves passing the nonwoven web through a first pair of nip rolls and over a plurality of heated rolls in a series of reverse S-loops to heat the web to the softening temperature of the web. The temperature of the heated rolls and the residence time of the web will vary, depending on the basis weight of the web and the polymer from which the web was made. For example, a meltblown polypropylene fiber web may be passed over a series of steam cans heated to a surface temperature from about 90° C. to about 150° C. for a contact time of about 1 to about 300 seconds to heat the web to a temperature above its softening point. Other suitable nonwoven web heating processes that may be utilized include infrared radiation, heated air, microwave radiation, ultrasonic energy, and convection ovens. The heated web then is passed through a second pair of nip rolls. The peripheral linear speed of the first pair of nip rolls is controlled to be less than the peripheral linear speed of the second pair of nip rolls so as to apply a neck-stretching tension. By controlling the linear speed differential between the two pair of nip rolls, the heated web may be necked to a desired extent. Optionally, the heated rolls may be controlled to have a linear speed or a series of linear speeds that are intermediate of the speeds of the two pair of nip rolls in order to facilitate the neck-stretching process. In addition to the nip roll arrangements, other tension-applying methods and apparatus known in the art can be utilized, e.g., tenter frames and godet rolls. The neck-stretched web is maintained under tension until it is cooled to retain the aligned configuration. The cooling process may be enhanced by the use of chilled air or chill rolls.

The fiber alignment ratio of a neck-stretched nonwoven web is a function of the degree or extent of neck-stretching. For example, an average fiber alignment ratio for a 50 percent neck-stretched meltblown polypropylene nonwoven web similar to that employed in the examples typically is about 40:1, whereas an average ratio for a 30 percent neck-stretched meltblown polypropylene nonwoven web typically is about 17:1.

As a further example, the fibrous web may be a web formed by hydraulic spinning. Such a web is composed of filaments which are almost completely oriented in the machine direction; see U.S. Pat. No. 5,244,723 to Anderson, which patent is incorporated herein by reference. Because of the high degree of machine direction orientation of the filaments, it may be desirable to employ a hydraulically spun web in conjunction with one or more support webs. For example, a hydraulically spun web may be bonded to another nonwoven web, such as a meltblown, coformed, spunbonded, or carded and bonded web. Alternatively, a hydraulically spun web may be sandwiched between two other nonwoven webs, either or both of which may be a meltblown web or a neck-stretched, meltblown web.

In general, the fibers of the fibrous web may be of any composition. As a practical matter, the fibers will be prepared from synthetic materials. Synthetic materials include thermosetting and thermoplastic polymers. The term "polymer" is meant to include blends of two or more polymers and alternating, random, block, and graft copolymers prepared from two or more different starting materials or monomers.

Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyderesins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acid), poly(ethyl acrylate), poly(methyl methacrylate), polyacrylonitrile, and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly($\epsilon$-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxy-1,4-phenylenesulfonyl-4,4'-biphenylene), and the like; polycarbonates, such as poly(bisphenol A) or poly(carbonyldioxy-1,4-phenyleneisopropylidene-1,4-phenylene), and the like; polyesters, such as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly(2-butene), poly(1-pentene), poly(2-pentene), poly(3-methyl-1-pentene),poly(4-methyl-1-pentene), and the like; vinyl polymers, such as poly(vinyl acetate), poly(vinylidene chloride), poly(vinyl chloride), and the like; diene polymers, such as 1,2-poly-1,3-butadiene, 1,4-poly-1,3-butadiene, polyisoprene, polychloroprene, and the like; polystryrenes; copolymers of the foregoing, such as acrylonitrile-butadiene-styrene (ABS) copolymers, and the like; and the like.

Desirably, the material will be composed of fibers prepared from a thermoplastic polymer. More desirably, the thermoplastic polymer will be a polyolefin. Examples of thermoplastic polyolefins include polyethylene, polypropylene, poly(1-butene), poly(2-butene), poly(1-pentene), poly(2-pentene), poly(3-methyl-1-pentene), poly(4-methyl-1-pentene), and the like. In addition, such term is meant to include blends of two or more polyolefins and random and block copolymers prepared from two or more different unsaturated monomers. Because of their commercial importance, the most desirable polyolefins are polyethylene and polypropylene.

As already noted, the fibrous web of the present invention includes a first zone composed of fibers which have been treated with a surfactant and a second zone composed of fibers which have been exposed to a corona field. At least one of the first zone and the second zone constitutes less than all of the fibrous web.

The term "zone" is used herein to mean the fibers constituting a given portion or volume of the fibrous web. Thus, a zone will have a length, a width, and a thickness, each of which may be equal to or less than the length, width, and thickness, respectively, of the fibrous web.

The fibers within the first zone have been treated with a surfactant. Desirably, the surfactant will be a nonionic surfactant. In certain embodiments, the surfactant is adapted to impart to the fibers increased wettability characteristics as a result of exposure of surfactant-treated fibers to a corona field. For example, when the fibers are prepared from polypropylene, the surfactant may be a polyethoxylated alkyl-substituted phenol. In other embodiments, the surfactant is adapted to have an increased affinity for the fibers of which the fibrous web is composed as a consequence of first exposing the fibers to a corona field. For example, when the fibers are prepared from polypropylene, the surfactant may be a polysiloxane polyether.

An amount of surfactant typically will be employed which is sufficient to achieve the desired distribution and/or retention effect. Such amount can vary widely. As a practical matter, the amount of surfactant present on the fibers in the first zone will be in a range of from about 0.1 to about 5 weight percent, based on the weight of the fibers. Desirably, the amount of surfactant present on the fibers will be in a range of from about 0.3 to about 3 weight percent.

Turning now to the second zone, the fibers therein are exposed to a corona field. As used herein, the term "corona field" means a corona field of ionized gas. In general, the generation of a corona field and exposure of the fibers are accomplished in accordance with procedures which are well known to those having ordinary skill in the art. The dose or energy density to which the fibers are exposed can range from about 1 to about 500 watt-minute per square foot (w-min/ft$^2$), which is approximately equivalent to a range of from about 0.6 to about 323 kilojoules per square meter (kJ/m$^2$). Desirably, such dose will be in a range of from about 15 to about 350 w-min/ft$^2$ (from about 10 to about 226 kJ/m$^2$).

In general, the orienting of fibers in the material (if carried out after formation of the material), the treatment of the fibers with a surfactant, and the exposure of the fibers to a corona field may be carried out in any order. Most commonly, a fibrous web will be treated first in whole or in part with surfactant to form a first zone. The web, or a portion thereof, as appropriate, then is exposed to a corona field to form a second zone. Thus, the present invention provides a method of preparing a fibrous web which involves the steps of providing a material comprised of fibers, treating at least a portion of the fibers with a surfactant, and exposing a at least a portion of the fibers to a corona field. Desirably, the fibers comprising the web will be at least partially oriented in one direction.

Alternatively, a fibrous web may be exposed to a corona field in whole or in part to form a second zone. The web, or a portion thereof, as appropriate, then is treated with surfactant to form a first zone. In this case, the method of the present invention involves the steps of providing a material comprised of fibers, exposing a portion of the fibers to a corona field, and treating at least a portion of the fibers with a surfactant. Desirably, the fibers comprising the web will be at least partially oriented in one direction.

If desired, a portion of the fibers may be treated with a first surfactant and another or different portion of the fibers may be treated with a second surfactant. Moreover, all or only part of the fibers of the medium may be exposed to a corona field. All of these permutations and combinations, as well as all others which will be apparent to those having ordinary skill in the art, are deemed to come within the spirit and scope of the present invention.

Figure 1:
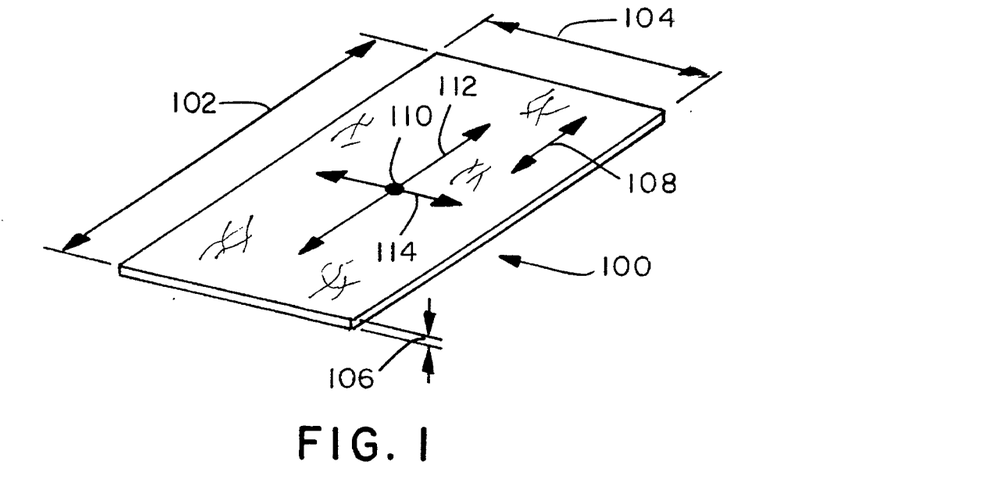
FIG. 1 is a diagrammatic perspective view of a portion of a liquid transport medium of the present invention.

When a liquid is applied to a fibrous web of the present invention, the liquid will flow away from the application site. For a web composed of oriented fibers, the direction of flow preferentially will be in the direction of orientation. This concept is more easily demonstrated with reference to FIG. 1. FIG. 1 shows a diagrammatic perspective view of a portion of a fibrous web 100 of the present invention. The fibrous web 100 has a length 102, a width 104, and a thickness 106. The direction of orientation of the fibers of which the medium 100 is composed is represented by line 108. When a liquid impinges the fibrous web 100 at a location 110, the liquid moves through the fibrous web away from the location 110. The maximum movement of liquid which is essentially parallel with the direction of orientation of the fibers is represented by the line 112. The maximum movement of liquid which is essentially normal to the direction of orientation of the fibers is represented by the line 114. The liquid distribution aspect ratio is the length of line 112 divided by the length of line 114.

Because the fibrous web is particularly well suited for use as a component of such absorbent product as diapers, incontinent care products, and feminine care products, the fibrous web generally will have a length which is greater than its width. In other words, with reference to FIG. 1, the length 102 generally will be greater than the width 104. Consequently, each of the first and second zones typically will have a length which is greater than its width. When the second zone of the fibrous web has a length which is greater than its width, the direction of flow of the applied liquid preferentially will be in a direction which is parallel with the length of the second zone. Consequently, the direction of orientation of the fibers of which the fibrous web is composed and the length of the second zone desirably will coincide in order to maximize distribution of the liquid lengthwise throughout the second zone.

In the examples, the lengthwise direction of the second zone always coincides with the lengthwise direction of the fibrous web. For this reason, it is convenient to consider the location 110 of fluid application as the origin of a set of Cartesian coordinates in a plane defined by a surface of the fibrous web. The y-axis of the coordinates is parallel with the length 102 and the x-axis is parallel with the width 104 of the fibrous web 100. Movement of fluid in a direction parallel with the length of the fibrous web (or with the length of the second zone) may be described as movement in the "y-direction."

As already noted, exposing the fibers to a corona field either (a) increases the wettability characteristics of a surfactant with which the fibers had been treated or (b) increases the affinity of the fibers for a surfactant with which the fibers subsequently are treated. Consequently, distribution and retention may be controlled by the selection of surfactant. Distribution and retention also may be controlled by how the fibers are exposed to a corona field.

By way of illustration of the foregoing principles, a fibrous web prepared from a polyolefin, e.g., polypropylene, may be treated with a surfactant, e.g., a polyethoxylated alkylphenol. Thus, the first zone constitutes all of the fibrous web. The surfactant-treated web then may be masked before being exposed to a corona field, thereby resulting in a second zone which is less than all of the fibrous web. For example, the mask may have an opening which is rectangular in shape, with the longer direction of the rectangular opening being essentially parallel with the direction of orientation of the fibers of which the fibrous web is composed. If the fibrous web is a meltblown nonwoven web, the movement of liquid which impinges the web in the second zone generally will result in an aspect ratio of at least about 2. If the fibrous web is a neck-stretched, meltblown nonwoven web, the movement of liquid which impinges the web in the second zone generally will result in an aspect ratio greater than about 3.

The fibrous web of the present invention also exhibits significantly increased liquid retention when compared with a similar web which lacks the second zone. In general, the fibrous web of the present invention will retain at least about 1.5 times as much liquid as a similar web which lacks the second zone. For example, the fibrous web may retain at least about twice as much liquid as the similar web. As another example, the fibrous web may retain at least about three times as much liquid as the similar web. As a further example, the fibrous web may retain at least about four times as much liquid as the similar web.

The present invention is further described by the examples which follow. Such examples, however, are not to be construed as limiting in any way either the spirit or the scope of the present invention.

EXAMPLE 1

A meltblown polypropylene nonwoven web was prepared on pilot scale equipment essentially as described in U.S. Pat.

No. 4,663,220 to Wisneski and Morman; the web had a basis weight of 1.5 ounces per square yard or osy (about 51 grams per square meter or gsm). The polypropylene employed was Type PF-015 (Himont Incorporated, Wilmington, Del.). The web was neck-stretched 50 percent as described earlier. The heated rolls were steam cans having a diameter of about 24 inches (about 61 cm) and heated at a temperature of about 113° C. The linear speed of the web at the first pair of nip rolls was about 36 feet per minute (about 18 cm per second). The web was passed over the steam cans at a linear speed of about 45 feet per minute (about 23 cm per second) and through the second pair of nip rolls at a linear speed of about 62 feet per minute (about 31 cm per second).

The neck-stretched web was cut into 7-inch×10-inch (about 18-cm×25-cm) pieces (cross direction or CD × machine direction or MD). Triton®X-102, a polyethoxylated octylphenol surfactant (Rohm and Haas Company, Philadelphia, Pa.) was topically applied to the pieces of nonwoven web at a level of 0.5 to 0.6 percent add-on by individually soaking the pieces for about three minutes in 500 ml of a deionized water solution containing 0.12 weight percent of the Triton® X-102. Two pieces were soaked per 500 ml of surfactant solution. After soaking in the surfactant solution, the pieces were passed through an Atlas Laboratory Wringer (Atlas Electric Devices Company, Chicago, Ill.) with a 30-pound nip setting and then dried in a fume hood.

Figure 2:
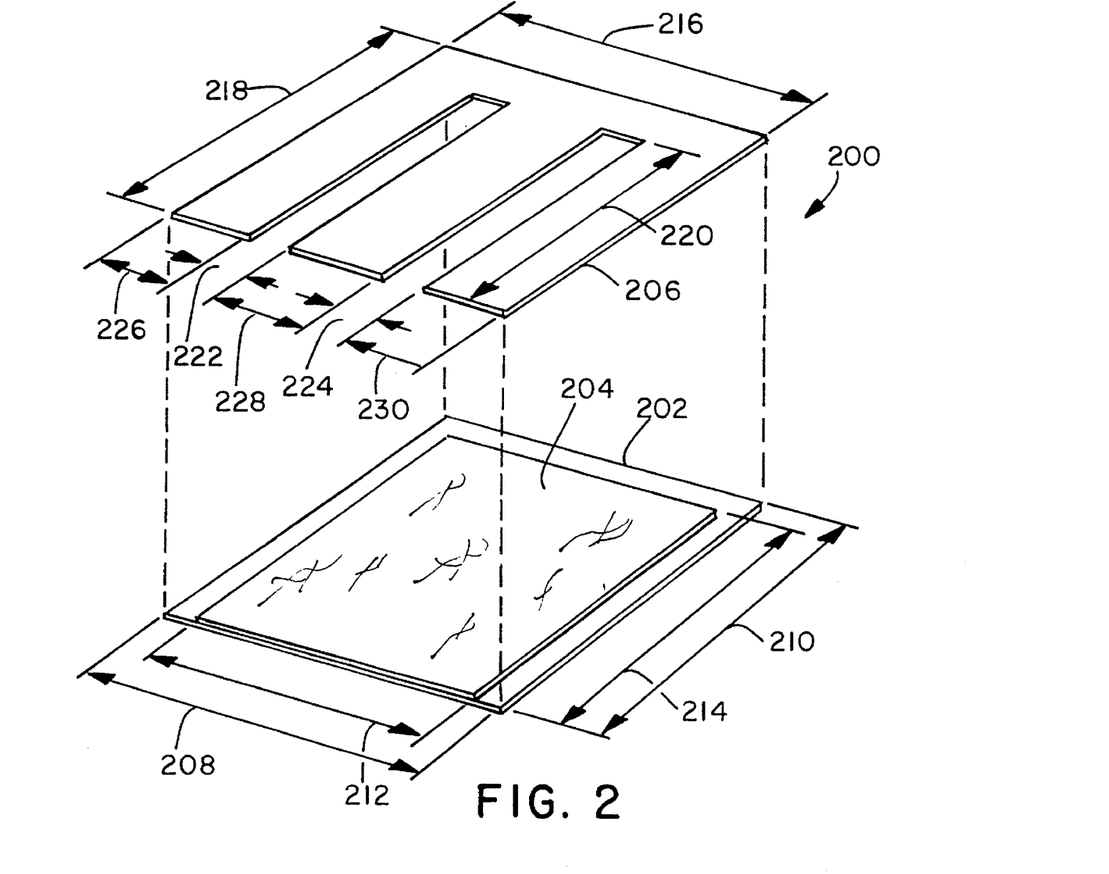
FIG. 2 is a diagrammatic perspective view of an assembly consisting of a carrier sheet, a fibrous web, and a corona mask as described in Example 1.

Some of the dried pieces of surfactant-treated, 50-percent neck-stretched meltblown polypropylene nonwoven web were exposed to a zoned corona field. Such zoned corona exposure was accomplished by taping each piece of nonwoven web to a carrier sheet, covering the web with a mask as shown in FIG. 2, and passing the resulting assembly through a corona field. FIG. 2 shows an assembly 200 which consists of a carrier sheet 202, a piece of a nonwoven web 204, and a mask 206. The carrier sheet 202 was an 8-inch× 12-inch (about 20-cm ×30-cm) piece of an EarthWise™ brand file folder. A shorter (CD) edge of the piece of nonwoven web 204 was placed on the carrier sheet so that such shorter edge was contiguous with a shorter edge of the carrier sheet 202 and the longer (MD) edges of the web were parallel with and equidistant from the longer edges of the carrier sheet. The corners of the web defined by the longer edges thereof and the other shorter edge were fastened to the carrier sheet 202 with two small pieces of tape (Highland™ brand, 3M Company, St. Paul, Minn.). The corona mask was made by taping two file folders together and cutting out two rectangular sections as shown. The mask resulted in a zone of corona treatment by limiting the corona exposure to the portions of the web which were situated below the two rectangular openings in the mask. Both sides of the web were exposed to the corona field, which required removing the web from the carrier sheet, turning the sheet over, and taping the sheet in place as already described. The dimensions of the carrier sheet 202, the nonwoven web 204, and the mask 206 are given in Table 1, with reference to FIG. 2.

TABLE 1

| | Dimensions Applicable to FIG. 2 | |
| --- | --- | --- |
| | Dimension | |
| Designation | Inches | cm |
| 208 | 8 | 25.4 |
| 210 | 12 | 30.5 |
| 212 | 7 | 17.8 |
| 214 | 10 | 25.4 |
| 216 | 8 | 25.4 |
| 218 | 12 | 30.5 |
| 220 | 11 | 27.9 |

TABLE 1-continued

| | Dimensions Applicable to FIG. 2 | |
| --- | --- | --- |
| | Dimension | |
| Designation | Inches | cm |
| 222 | 0.75 | 1.9 |
| 224 | 0.75 | 1.9 |
| 226 | 2 | 5.1 |
| 228 | 2.5 | 6.4 |
| 230 | 2 | 5.1 |

The corona field was generated by means of a Corotec Laboratory Corona Treating Station with a CXC-5 Power Supply (Corotec Corporation, Collinsville, Conn.). The Treating Station utilized a pair of rotating metal rolls as electrodes, with the axes of the rolls lying in a vertical plane. Both rolls had a circumference of 12 inches (about 30.5 cm) and a diameter of about 3.8 inches (about 9.7 cm). The top roll was the anode and the bottom roll was the cathode. The bottom roll was fitted with a 2-mm-thick rubber dielectric sleeve which was in contact with the top roll, thereby providing a space of 2 mm between the electrodes. The top roll was 13 inches (about 33 cm) long and the bottom roll was about 16 inches (about 40.6 cm) long. The rolls rotated in opposite directions at a linear velocity of 12 feet per minute (about 6 cm per second).

The corona treatments were carried out in air at energy density levels of 12 to 220 kilojoules per square meter (kJ $m^{-2}$) per side of nonwoven web. The energy density refers to the energy absorbed as a function of electrode width and the rate at which the web passes through the corona field. Energy density is calculated by dividing the output power in kilowatts by the width of the electrodes in meters and then by the line speed in meters per second, followed by multiplying the resulting value by the number of times the web passes between the electrodes. The result is energy density in kilowatt-second per square meter, which is equivalent to kilojoules per square meter. Four different fibrous webs were prepared, as summarized in Table 2; in the table, corona energy density values are given in kJ $m^{-2}$.

TABLE 2

| | Summary of Fibrous Web Treatments | |
| --- | --- | --- |
| Web | Surfactant Add-on (wt-%) | Corona Energy Density |
| 1-A | 0.6 | 0 |
| 1-B | 0.5 | 22 |
| 1-C | 0.6 | 116 |
| 1-D | 0.5 | 220 |

Each surfactant-treated piece of nonwoven web, whether exposed to a corona field or not, was cut in half, with the cut being parallel with the longer edges. This cut created two 3.5-inch×10-inch (about 9-cm×25-cm) pieces. Each piece then was trimmed by removing the "top" 2 inches (about 5 cm), thereby creating a piece 3.5 inches×8 inches (about 9 cm×13 cm). For pieces exposed to a corona field, the "top" portion was the portion at the end which was taped to the carrier sheet.

The web pieces with topically-applied Triton® X-102 surfactant and various levels of zoned corona exposure, including no corona exposure, then were tested for blood wicking characteristics. Testing was carried out in each case by removing the liner or cover from a Kotex® Maxi Pad (Kimberly-Clark Corporation, Neenah, Wis.) and reassembling the pad by placing the piece of nonwoven web to be tested on top of the absorbent core of the Pad. Pieces that were exposed to the zoned corona field were placed on top of the Kotex® Pad absorbent core with the ¾-inch wide zoned region situated approximately in the middle of the pad.

The reassembled Maxi Pad was placed on top of a water-filled colostomy bag which in turn was placed on a laboratory jack. An opening in the colostomy bag was connected to a manometer. The laboratory jack was raised to bring the Maxi Pad assembly against a plexiglass plate at a pressure of 0.3 pounds per square inch gauge (psig). The plate had a hole drilled through it, in which a blunt needle was located. The Maxi Pad assembly was oriented against the plate so that the needle in the plate was in the approximate center of the web covering the Pad. The needle was connected by a thin tube to a syringe containing bovine blood. The syringe was driven by a syringe pump set to deliver approximately 4 ml of fluid per hour. However, the actual amount of blood delivered is somewhat dependent on the resistance encountered as the blood moves from the syringe and through the thin tube to the plexiglass plate. The bovine blood was pumped onto the web covering each Maxi Pad for 30 minutes. All components of the Maxi Pad assembly (i.e., web and Maxi Pad absorbent core) were weighed before and after each experiment to determine the amount of blood retained by each component. Also, the dimensions of the blood stain on the web were measured after each experiment in order to calculate the aspect ratio.

Tables 3 and 4 summarize the blood distribution and/or retention characteristics for the fibrous web and absorbent core of the Maxi Pad for the blood wicking experiments, identified by the fibrous web employed, i.e., Experiments 1-A, 1-B, 1-C, and 1-D. The weights of each component before and after the blood wicking experiments are presented in Table 3. The amount of blood retained by each component (Comp.) is given in Table 4, both as an amount and as a percent of the total amount of blood present in both components, i.e., Percent=100×[Comp. Amt./(Web Amt.+Core Amt.)]

All weights listed in Table 3 are in grams (g). The aspect ratio for each experiment was calculated and is included in Table 4. Table 4 also includes the y-direction distribution distance measurement.

TABLE 3

Bovine Blood Wicking Results (Weights)

| Expt. | Component | Initial Wt. (g) | Final Wt. (g) |
| --- | --- | --- | --- |
| 1-A | Web | 1.112 | 1.252 |
|  | Core | 11.781 | 13.640 |
| 1-B | Web | 0.970 | 1.516 |
|  | Core | 10.322 | 11.727 |
| 1-C | Web | 0.925 | 1.467 |
|  | Core | 11.601 | 12.988 |
| 1-D | Web | 0.974 | 1.502 |
|  | Core | 11.915 | 13.278 |

TABLE 4

Bovine Blood Wicking Results (Calculations and Measurements)

| Expt. | Component | Difference Amount | Difference Percent | Aspect Ratio | y-Dir. (cm) |
| --- | --- | --- | --- | --- | --- |
| 1-A | Web | 0.140 | 7.0 | 1.2 | 5.0 |
|  | Core | 1.859 | 93.0 | N/R[a] | N/R |
| 1-B | Web | 0.546 | 28.0 | 5.9[b] | 11.8 |
|  | Core | 1.405 | 72.0 | N/R | N/R |
| 1-C | Web | 0.542 | 28.1 | 6.2 | 12.5 |
|  | Core | 1.387 | 71.9 | N/R | N/R |
| 1-D | Web | 0.528 | 27.9 | 6.2[b] | 13.5 |
|  | Core | 1.363 | 72.1 | N/R | N/R |

[a]Not relevant. The distribution pattern of blood in the core generally reflected the distribution pattern of the web. However, the correlation of the core distribution pattern with that of the web was only approximate because the surface of the core adjacent to the web was not smooth due to the presence of wrinkles or fold lines. Moreover, the core was designed for absorbency, not distribution. Thus, aspect ratio calculations and y-direction measurements for the core were considered not relevant to the present invention.
[b]The aspect ratio for the majority of the blood present in the web. See the discussion following this table.

From Experiments 1-B, 1-C, and 1-D, it is evident that a zoned corona post-treatment leads to increased blood retention in the web. In each instance, the amount of blood retained by the fibrous web was four times that of Web 1-A, a web similar to each of Webs 1-B, 1-C, and 1-D but lacking the second zone.

Experiments 1-B, 1-C, and 1-D also demonstrate that the zoned corona post-treatment resulted in greater blood distribution in the web. In each case, an approximately five-fold increase in the aspect ratio was obtained. Note that the y-direction distribution distance more than doubled.

Figure 3:
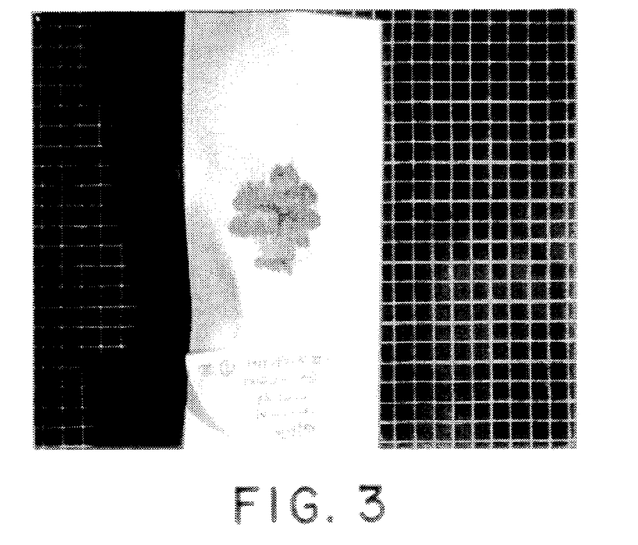
FIGS. 3–13, inclusive, are photographs of webs of the present invention at the conclusion of blood wicking experiments as described in the examples.
Figure 4:
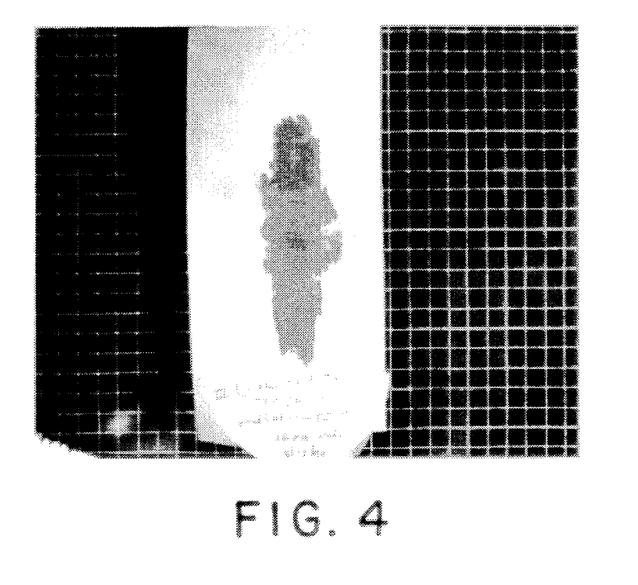
Figure 5:
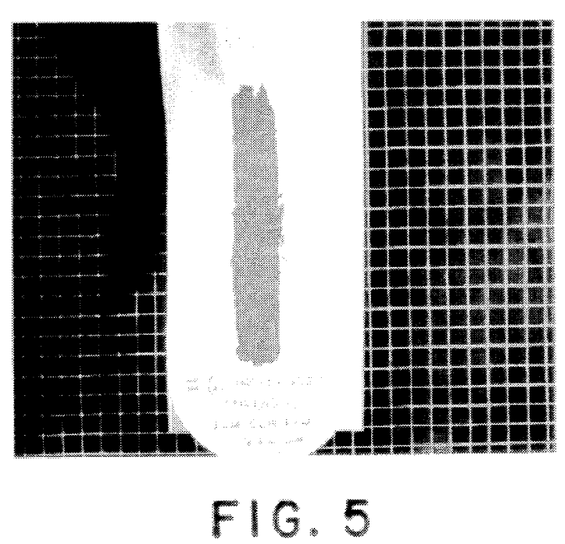
Figure 6:
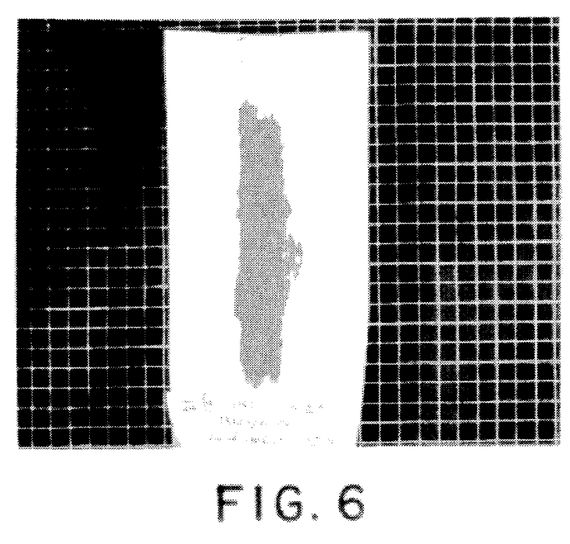

In order to better illustrate the improved distribution which results with fibrous webs of the present invention, i.e., the increases in both aspect ratios and y-direction distribution distances, photographs of Webs 1-A through 1-D at the conclusion of the blood wicking experiments are shown in FIGS. 3–6, respectively. From Table 2, it is seen that each of Webs 1-A through 1-D has a first zone which consists of all of the fibrous web. Web 1-A, however, does not have a second zone and gave an aspect ratio of 1.2. It is seen in FIG. 3 that the blood distribution pattern is roughly circular; that is, the distribution of the blood in the long or machine direction of the web is only slightly better that the that in the short or cross direction of the web. In FIGS. 4–6, the elongated fluid distribution patterns are readily apparent. Also apparent from the darker fluid images in these figures is the increased fluid retention.

Each of Webs 1-B, 1-C, and 1-D has a second zone which consists of a portion of the fibers of the first zone. In each case, the second zone is a 0.75-inch (approximately 2-cm) wide region which is parallel with the longer direction of the web and located approximately equidistant from the longer edges of the web. The second zones differ only in the energy density of the corona fields to which the second zones were exposed.

From FIGS. 4–6, inclusive, it is evident that a remarkable improvement in the distribution of blood in a direction parallel with the longer direction of the web, i.e., in the machine direction, has been achieved, even at an energy density of as little as 22 kJ m$^{-2}$. With Web 1-B, the aspect ratio for the majority of the blood was 5.9, the value reported in Table 4. If the aspect ratio is calculated using the maximum movement of blood in the cross direction, a value of 3.4 is obtained (see FIG. 4). FIG. 5 illustrates that for Web 1-C essentially all of the blood was distributed only within the second zone, i.e., the portion of the first zone which had been exposed to the corona field, thereby giving rise to an aspect ratio of 6.2. FIG. 6 shows that most of the blood was distributed within the second zone of Web 1-D, and only a few small streaks of blood were distributed outside of the second zone occurred.

Either or both of two phenomena may be contributing to the cross direction distribution observed with Webs 1-B and 1-D. First, the masking method may permit some exposure to the corona field of fibers under the mask. Second, the distribution of blood in the cross direction may be rate related. The results seen with Web 1-C (FIG. 5) suggest that the first phenomenon is more likely since a rate-related phenomenon should have resulted in some cross direction distribution with all three webs instead of just with Webs 1-B and 1-D.

EXAMPLE 2

The procedure of Example 1 was repeated, except that the pieces of nonwoven web were exposed first to a zoned corona field and then treated with a polysiloxane polyether surfactant instead of Triton® X-102. The polysiloxane polyether had the following structural formula:

The surfactant had a number-average molecular weight of about 6,000, a weight-average molecular weight of about 11,100, and a z-average molecular weight of about 16,000. The polydispersity of the surfactant was 1.85. Treatment of the webs with the surfactant involved immersing them in 500 ml of a deionized water solution containing 0.25 weight-percent of the surfactant. The pieces were immersed in the surfactant solution within 5 minutes of the corona pre-treatment and the immersion time varied from about 30 seconds to 2 minutes, depending on the level of corona exposure. The surfactant solution was observed to preferentially wet-out the webs in the zones which were exposed to the corona field. After being immersed in the surfactant solution, the pieces were hung in a fume hood to dry. The add-on level of surfactant was not measured. Three different fibrous webs were prepared, as summarized in Table 5; in the table, corona energy density values are given in kJ m$^{-2}$.

TABLE 5

Summary of Fibrous Web Treatments

| Web | Surfactant Add-on (wt-%) | Corona Energy Density |
|---|---|---|
| 2-A | N/D | 66 |
| 2-B | N/D | 110 |
| 2-C | N/D | 220 |

The pieces then were tested for blood wicking characteristics as described in Example 1. Tables 6 and 7 summarize the blood distribution and/or retention characteristics for components of Maxi Pad assemblies (i.e., web pieces and underlying absorbent cores) after the blood wicking experiments.

TABLE 6

Bovine Blood Wicking Results (Weights)

| Expt. | Component | Initial Wt. (g) | Final Wt. (g) |
|---|---|---|---|
| 2-A | Web | 0.883 | 1.170 |
|  | Core | 11.765 | 13.330 |
| 2-B | Web | 0.944 | 1.307 |
|  | Core | 10.575 | 12.118 |
| 2-C | Web | 0.932 | 1.272 |
|  | Core | 10.225 | 11.696 |

TABLE 7

Bovine Blood Wicking Results (Calculations and Measurements)

| Expt. | Component | Difference Amount | Difference Percent | Aspect Ratio | y-Dir. (cm) |
|---|---|---|---|---|---|
| 2-A | Web | 0.287 | 15.5 | 3.8 | 8.8 |
|  | Core | 1.565 | 84.5 | N/R[a] | N/R |
| 2-B | Web | 0.363 | 19.0 | 3.2 | 9.8 |
|  | Core | 1.543 | 81.0 | N/R | N/R |
| 2-C | Web | 0.340 | 18.8 | 3.5 | 9.8 |
|  | Core | 1.471 | 81.2 | N/R | N/R |

[a]Not relevant. See footnote a of Table 4.

From the data in Tables 6 and 7, it is apparent that the zoned corona pre-treatment followed by a polysiloxane polyether surfactant post-treatment produces webs that are effective at distributing blood. In each case, the aspect ratio was greater than 3 and the y-direction distribution distances were significant, ranging from 8.8 cm to 9.8 cm. Without wishing to be bound by theory, it was postulated that the results seen in Tables 6 and 7 resulted from an increased affinity in the corona pre-treated zone of the surfactant for the polypropylene fibers of which the web was composed. In order to test this postulate, drops of water were placed on each web, both in the corona pre-treatment zone and in an area of the web not exposed to a corona field. In each case, the drops of water placed in the corona pre-treatment zone penetrated into the web instantly. Outside of the corona pre-treatment zone, however, several of the drops of water penetrated the web only after 1–2 seconds, while the majority of the drops of water either spread or remained beaded after 1 minute. Although the entire web in each case was exposed to the surfactant solution, adherence of the surfactant to the web outside of the corona pre-treatment zone appeared to be minimal.

Figure 7:
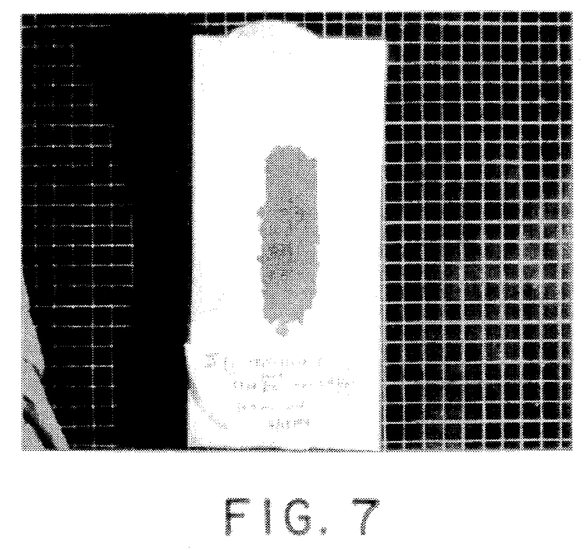
Figure 8:
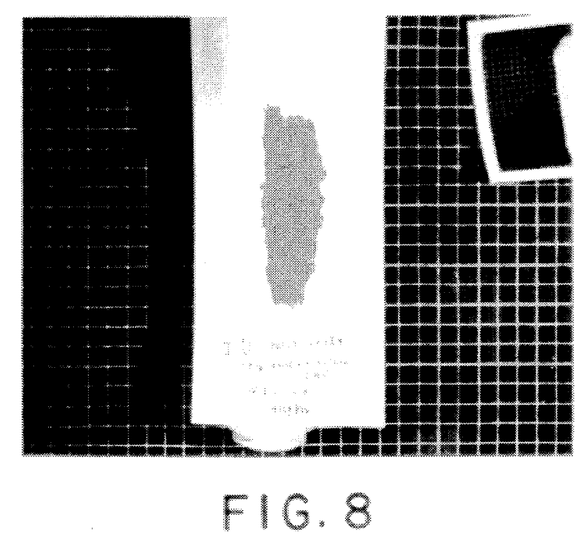
Figure 9:
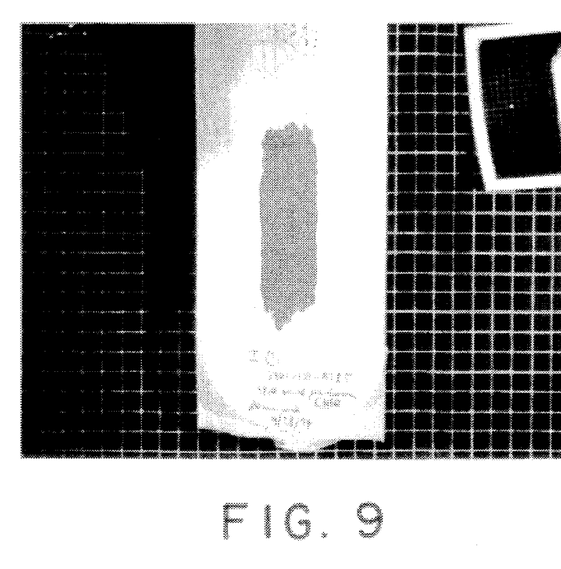

In order to again better illustrate the improved distribution which results with fibrous webs of the present invention, photographs of Webs 2-A through 2-C at the conclusion of the blood wicking experiments are shown in FIGS. 7–9, respectively. Each of Webs 2-A, 2-B and 2-C has a second zone which consists of a portion of the fibers of the first zone. Again, the second zone is a 0.75-inch (approximately 2-cm) wide region which is parallel with the longer direction of the web and located approximately equidistant from the longer edges of the web. The second zones differ only in the energy density of the corona fields to which the second zones were exposed. However, each of the second zones was formed before the first zones were formed. From FIGS. 7–9, it is seen that essentially all of the blood was distributed in the second zone of the web.

As noted above, it is believed by forming the first zone after forming the second zone, the surfactant adhered to or had an affinity for only those fibers in the second zone. Consequently, the first zone and second zones are contiguous. That is, both zones involve the same fibers and are less than all of the fibrous web.

EXAMPLE 3

A meltblown polypropylene nonwoven web having a basis weight of 1.5 osy (about 51 gsm) was neck-stretched by 30 percent as described in Example 1, except that the linear speeds through the first pair of nip rolls, over the steam cans, and through the second pair of nip rolls were 41 feet per minute (about 21 cm per second), 45 feet per minute (about 23 cm per second), and 53 feet per minute (about 27 cm per second), respectively. The neck-stretched web was cut into 7-inch by 10-inch (about 18-cm×25-cm) pieces. One set of samples (Webs 3-A and 3-B) was cut with the 7-inch dimension being in the cross direction (CD) of the web while the other set (Webs 3-C and 3-D) was cut with that dimension being in the machine direction (MD). Thus, the direction of orientation of the fibers in Webs 3-A and 3-B is parallel with the longer direction of the fibrous web, while the direction of orientation of the fibers in Webs 3-C and 3-D is normal to the longer direction of the fibrous web. Triton® X-102 surfactant was topically applied to the web pieces at a level of 0.6 to 0.7 weight percent dry add-on by individually soaking the web pieces for 2 minutes as described in Example 1.

Some of the dried pieces of surfactant-treated web were exposed to a zoned corona field as described in Example 1. Four different fibrous webs were prepared, as summarized in Table 8; in the table, corona energy density values are given in kJ m$^{-2}$.

TABLE 8

Summary of Fibrous Web Treatments

| Web | Surfactant Add-on (wt-%) | Corona Energy Density |
|---|---|---|
| 3-A | 0.7 | 0 |
| 3-B | 0.7 | 116 |
| 3-C | 0.7 | 0 |
| 3-D | 0.6 | 116 |

After corona exposure, the web pieces then were tested for blood wicking characteristics, also as described in Example 1. Tables 9 and 10 summarize the blood distribution and/or retention characteristics for components of Maxi Pad assemblies (i.e., web pieces and underlying absorbent cores) after the blood wicking experiments.

TABLE 9

Bovine Blood Wicking Results (Weights)

| Expt. | Component | Initial Wt. (g) | Final Wt. (g) |
|---|---|---|---|
| 3-A | Web | 0.99 | 1.18 |
|  | Core | 11.63 | 13.40 |
| 3-B | Web | 0.91 | 1.51 |
|  | Core | 11.77 | 13.08 |
| 3-C | Web | 0.91 | 1.19 |
|  | Core | 11.52 | 13.24 |
| 3-D | Web | 0.92 | 1.51 |
|  | Core | 11.92 | 13.36 |

TABLE 10

Bovine Blood Wicking Results (Calculations and Measurements)

| Expt. | Component | Difference Amount | Difference Percent | Aspect Ratio | y-Dir. (cm) |
|---|---|---|---|---|---|
| 3-A | Web | 0.19 | 9.7 | 1.0 | 5.5 |
|  | Core | 1.77 | 90.3 | N/R[a] | N/R |
| 3-B | Web | 0.60 | 31.4 | 6.5 | 13.0 |
|  | Core | 1.31 | 68.6 | N/R | N/R |
| 3-C | Web | 0.28 | 14.0 | 1.7 | 5.0 |
|  | Core | 1.72 | 86.0 | N/R | N/R |
| 3-D | Web | 0.59 | 29.1 | 0.7 | 10.0 |
|  | Core | 1.44 | 70.9 | N/R | N/R |

[a]Not relevant. See footnote a of Table 4.

From Experiments 3-A and 3-B, it is clear that the zoned corona post-treatment enhanced blood retention and distribution for 30-percent neck-stretched meltblown webs treated with Triton® X-102 surfactant, as evidenced by the 6.5-fold increase in aspect ratio and greater than doubled y-direction distribution distance for Web 3-B when compared to Web 3-A. Moreover, fluid retention was increased roughly three fold. Experiments 3-C and 3-D show that, even when the neck-stretched direction (i.e., the machine direction) of the web are aligned perpendicular to the long direction of the web and Kotex® Maxi Pad absorbent core, zoned corona exposure (always aligned parallel to the long direction of the Pad) still has a significant impact on the blood distribution. Such impact is demonstrated by both the reduction in the aspect ratio and two-fold increase in the y-direction distribution distance, from 1.7 and 5.0 cm, respectively, for Web 3-C to 0.7 and 10.0 cm, respectively, for Web 3-D. Fluid retention for Web 3-D was about two times that for Web 3-C.

Photographs of Webs 3-A through 3-D at the conclusion of the blood wicking experiments are shown in FIGS. 10–13, respectively. From Table 8, it is seen that each of Webs 3-A through 3-D has a first zone which consists of all of the fibrous web. Webs 3-A and 3-C, however, do not have a second zone.

Figure 10:
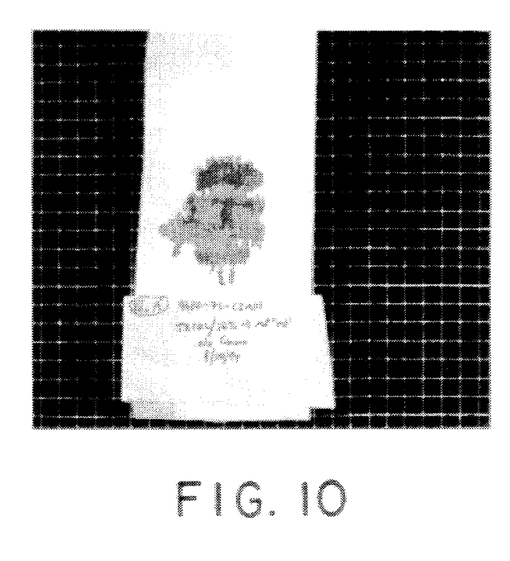
Figure 11:
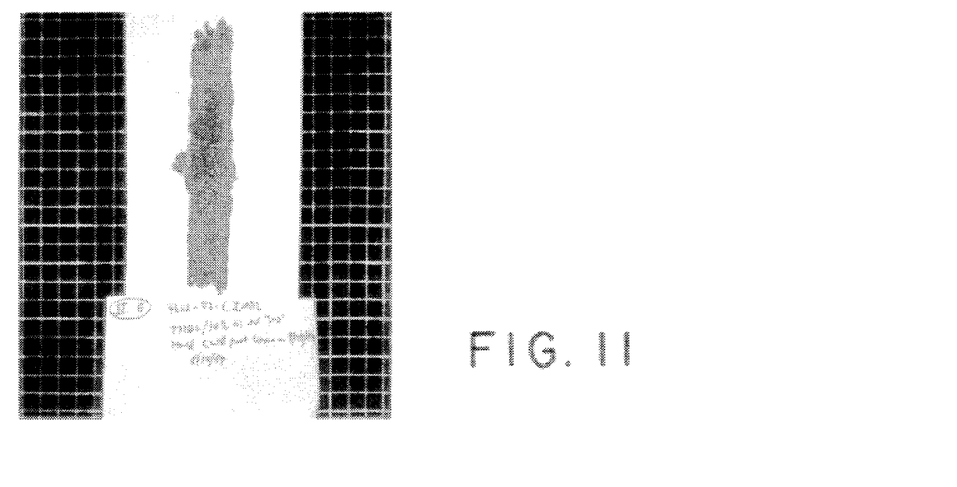

Web 3-A gave an aspect ratio of 1.0. While the pattern is irregular, FIG. 10 shows that the distance the blood moves in a direction parallel with the longer edges of the web is essentially the same as that in a direction normal to such edges, thereby giving rise to an aspect ratio of 1.0. FIG. 11 verifies the aspect ratio of 6.5 given in Table 10 for Web 3-B. That is, essentially all of the blood has been distributed within the second zone.

Each of Webs 3-B and 3-D has a second zone which consists of a portion of the fibers of the first zone. In each case, the second zone is an approximately 2-cm wide region which is parallel with the longer direction of the web and located approximately equidistant from the longer edges of the web. In each case, the energy density of the corona field was the same.

Figure 12:
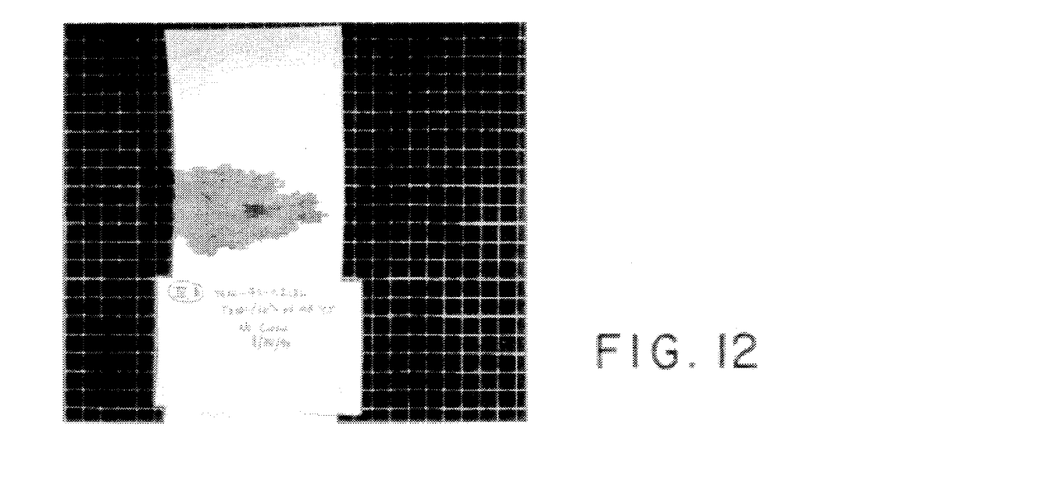
Figure 13:
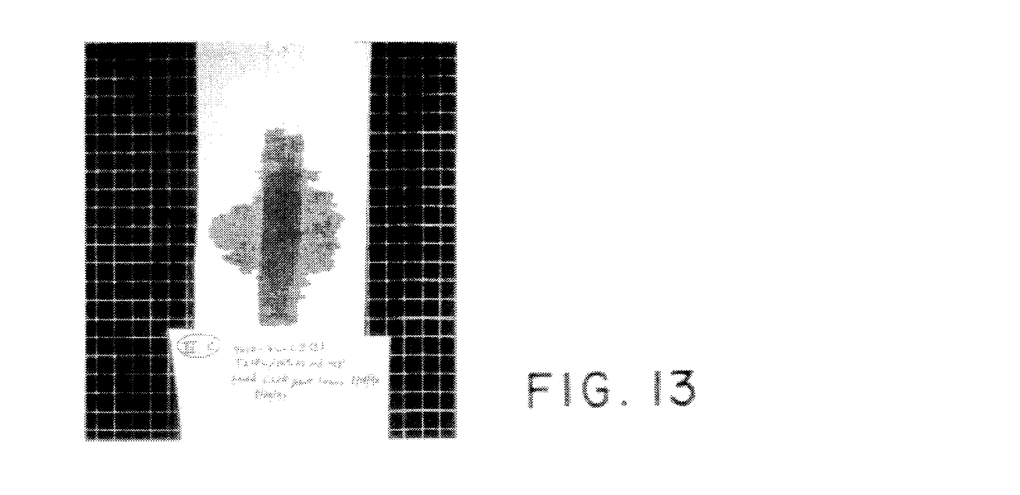

Webs 3-C and 3-D, it will be remembered, were cut so that the direction of orientation of the fibers was normal to the longer edges of the fibrous web. FIG. 12 demonstrates that, when the web lacks a second zone, the blood preferentially is distributed in a direction which is parallel with the direction of orientation of the fibers, i.e., normal to the longer edges of the web. FIG. 13 demonstrates the strong influence the second zone has on the distribution of the blood; notwithstanding the direction of orientation of the fibers, a y-direction distribution distance of 10.0 cm still was obtained.

EXAMPLE 4

The procedure of Example 1 was repeated with the standard meltblown polypropylene nonwoven web described in the previous examples. The web had a basis weight of 1.5 osy (about 51 gsm) and the polypropylene employed was Type HF-015 (Himont Incorporated, Wilmington, Del.).

Three webs were prepared as summarized in Table 11 (in the table, corona energy density values are given in kJ m$^{-2}$).

TABLE 11

Summary of Fibrous Web Treatments

| Web | Surfactant Add-on (wt-%) | Corona Energy Density |
|---|---|---|
| 4-A | 0.9 | 0 |
| 4-B | 0.9 | 0 |
| 4-C | 0.8 | 116 |

The webs then were tested for blood wicking characteristics as described in Example 1. Tables 12 and 13 summarize the blood distribution and/or retention characteristics for components of Maxi Pad assemblies (i.e., web pieces and underlying absorbent cores) after the blood wicking experiments.

TABLE 12

Bovine Blood Wicking Results (Weights)

| Expt. | Component | Initial Wt. (g) | Final Wt. (g) |
|---|---|---|---|
| 4-A | Web | 0.94 | 1.28 |
|  | Core | 11.84 | 13.56 |
| 4-B | Web | 0.95 | 1.41 |
|  | Core | 12.16 | 13.67 |
| 4-C | Web | 0.88 | 1.65 |
|  | Core | 11.71 | 12.88 |

TABLE 13

Bovine Blood Wicking Results (Calculations and Measurements)

| Expt. | Component | Difference Amount | Difference Percent | Aspect Ratio | y-Dir. (cm) |
|---|---|---|---|---|---|
| 4-A | Web | 0.34 | 16.5 | 1.4 | 8.5 |
|  | Core | 1.72 | 83.5 | N/R[a] | N/R |
| 4-B | Web | 0.46 | 23.4 | 1.0 | 7.7 |
|  | Core | 1.51 | 76.6 | N/R | N/R |
| 4-C | Web | 0.77 | 39.7 | 1.9 | 13.5 |
|  | Core | 1.17 | 60.3 | N/R | N/R |

[a]Not relevant. See footnote a of Table 4.

The average aspect ratio for Webs 4-A and 4-B, which served as controls, was 1.2. Web 4-C, on the other hand, had an aspect ratio of 1.9. The average amount of blood retained by the two control webs was about 20 percent of the total amount of blood to which each web was exposed. Web 4-C, however, retained about 40 percent of the total amount of blood to which it was exposed. Thus, the benefits of corona field exposure, i.e., the second zone, are readily apparent, even without neck-stretching the fibrous web to significantly orient the fibers in the y-direction.

EXAMPLE 5

The procedure of Example 3 with respect to Webs 3-C and 3-D was repeated, except that the fibrous web was the standard meltblown polypropylene nonwoven web employed in Example 4. Two webs were prepared as summarized in Table 14 (in the table, corona energy density values are given in kJ m$^{-2}$). In both webs, the direction of orientation of the fibers is normal to the longer direction of the fibrous web.

TABLE 14

Summary of Fibrous Web Treatments

| Web | Surfactant Add-on (wt-%) | Corona Energy Density |
|---|---|---|
| 5-A | 0.8 | 0 |
| 5-B | 0.8 | 116 |

The webs then were tested for blood wicking characteristics as described in Example 1. Tables 15 and 16 summarize the blood distribution and/or retention characteristics for components of Maxi Pad assemblies (i.e., web pieces and underlying absorbent cores) after the blood wicking experiments.

TABLE 15

Bovine Blood Wicking Results (Weights)

| Expt. | Component | Initial Wt. (g) | Final Wt. (g) |
|---|---|---|---|
| 5-A | Web | 1.00 | 1.13 |
|  | Core | 11.72 | 13.59 |
| 5-B | Web | 1.07 | 1.63 |
|  | Core | 12.22 | 13.49 |

TABLE 16

Bovine Blood Wicking Results
(Calculations and Measurements)

| Expt. | Component | Difference Amount | Percent | Aspect Ratio | y-Dir. (cm) |
|---|---|---|---|---|---|
| 5-A | Web | 0.13 | 6.5 | 1.4 | 4.5 |
|  | Core | 1.87 | 93.5 | N/R[a] | N/R |
| 5-B | Web | 0.56 | 30.6 | 0.8 | 11.0 |
|  | Core | 1.27 | 69.4 | N/R | N/R |

[a]Not relevant. See footnote a of Table 4.

Results similar to those obtained with Webs 3-C and 3-D were obtained with Webs 5-A and 5-B. When the web lacks a second zone, the blood preferentially is distributed in a direction which is parallel with the direction of orientation of the fibers, i.e., normal to the longer edges of the web. Note again the strong influence the second zone has on both the distribution and retention of the blood. Notwithstanding the direction of orientation of the fibers, a y-direction distribution distance of 11.0 cm still was obtained. In addition, blood retention was increased from 6.5 percent to almost 31 percent.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A fibrous web having a fiber alignment ratio of at least about 17:1 and which comprises:
   a first zone comprised of fibers which have been treated with a surfactant; and
   a second zone comprising less than all of the fibers of the web in which the fibers of the second zone have been exposed to a corona field;
   wherein the exposure of the web to the corona field is limited to the second zone, the first zone encompasses the entirety of the second zone, and the web is adapted to distribute liquid primarily in the direction of the orientation of the fibers.

2. The fibrous web of claim 1, in which the first zone is comprised of fibers which have been treated with a mixture of two or more surfactants.

3. The fibrous web of claim 1, in which the first zone comprises:
   a first portion of fibers which have been treated with a first surfactant; and
   a second portion of fibers which have been treated with a second surfactant.

4. The fibrous web of claim 1, in which the fibrous web comprises a neck-stretched meltblown nonwoven web.

5. The fibrous web of claim 1, in which the fibrous web is adapted to have a liquid distribution aspect ratio greater than about 3 when insulted with an aqueous liquid.

6. The fibrous web of claim 1, in which the fibrous web is adapted to retain at least about 1.5 times as much liquid as a similar web which lacks the second zone.

7. The fibrous web of claim 1, in which the fibrous web is adapted to retain at least about two times as much liquid as a similar web which lacks the second zone.

8. The fibrous web of claim 1, in which the surfactant is adapted to impart to the fibers increased wettability characteristics as a result of exposure of surfactant-treated fibers to the corona field.

9. The fibrous web of claim 1, in which the surfactant is adapted to have an increased affinity for the fibers of which the fibrous web is composed as a consequence of first exposing the fibers to a corona field.

10. The fibrous web of claim 9, in which the surfactant is a polysiloxane polyether.

11. The fibrous web of claim 1, in which the second zone has a longer dimension which is essentially parallel with the direction of orientation of the fibers of the fibrous web.

12. The fibrous web of claim 1, in which the first zone and the second zone involve essentially the same portion of the fibrous web.

13. An absorbent product having as a component thereof the fibrous web of claim 1.

14. An absorbent product having as a component thereof the fibrous web of claim 4.

15. The fibrous web of claim 1, in which the fiber alignment ratio is at least about 40:1.

16. The fibrous web of claim 5, in which the fibrous web is adapted to give a liquid distribution aspect ratio of at least about 5 when insulted with an aqueous liquid.

17. The fibrous web of claim 5, in which the fiber alignment ratio is at least about 40:1.

18. A method of preparing a liquid distribution and retention medium comprising the steps of:
   providing a fibrous web having a fiber alignment ratio of at least about 17:1;
   treating at least a portion of the fibrous web with a surfactant to form a first zone comprised of surfactant-treated fibers; and
   exposing less than all of the fibers of the web to a corona field to form a second zone;
   wherein the exposure of the web to the corona field is limited to the second zone, the first zone encompasses the entirety of the second zone, and the web is adapted to distribute liquid primarily in the direction of the orientation of the fibers.

19. The method of claim 18, in which the second zone has a longer dimension which is essentially parallel with the direction of orientation of the fibers comprising the fibrous web.

20. A method of preparing a liquid distribution and retention medium comprising the steps of:
   providing a fibrous web having a fiber alignment ratio of at least about 17:1;
   exposing less than all of the fibers of the web to a corona field to form a second zone; and
   treating at least a portion of the fibrous web with a surfactant to form a first zone comprised of surfactant-treated fibers;
   wherein the exposure of the web to the corona field is limited to the second zone, the first zone encompasses the entirety of the second zone, and the web is adapted to distribute liquid primarily in the direction of the orientation of the fibers.

21. The method of claim 20, in which the second zone has a longer dimension which is essentially parallel with the direction of orientation of the fibers comprising the fibrous web.

22. The method of claim 18, in which the fiber alignment ratio is at least about 40:1.

23. The method of claim 20, in which the fiber alignment ratio is at least about 40:1.

* * * * *

UNITED STATES PATENT AND TRADEMARK OFFICE
CERTIFICATION OF CORRECTION

PATENT NO. : 5,614,295

DATED : March 25, 1997

INVENTOR(S): Roger B. Quincy, III et al.

It is certified that error appears in the above-identified patent and that said Letters Patent is hereby corrected as shown below:

Column 4, line 48, "(Widths)" should read --($Width_i$)--;
Column 9, line 41, "web defined" should read --web 204 defined--.

Signed and Sealed this

Fifteenth Day of July, 1997

Attest:

BRUCE LEHMAN

Attesting Officer     Commissioner of Patents and Trademarks